United States Patent
Mopper

(10) Patent No.: US 6,783,366 B1
(45) Date of Patent: Aug. 31, 2004

(54) METHOD OF FINISHING RESIN-BASED DENTAL RESTORATIONS

(75) Inventor: K. William Mopper, Northbrook, IL (US)

(73) Assignee: Mo R&D, Inc., Chicago, IL (US)

(*) Notice: Subject to any disclaimer, the term of this patent is extended or adjusted under 35 U.S.C. 154(b) by 0 days.

(21) Appl. No.: 09/997,562

(22) Filed: Nov. 29, 2001

Related U.S. Application Data

(60) Provisional application No. 60/250,560, filed on Dec. 1, 2000.

(51) Int. Cl.[7] .................................................. A61C 5/04
(52) U.S. Cl. ........................................ 433/226; 264/16
(58) Field of Search .............................. 433/226, 228.1, 433/165, 166, 202.1; 264/16, 19, 20

(56) References Cited

U.S. PATENT DOCUMENTS

| | | | | |
|---|---|---|---|---|
| 3,872,593 A | * | 3/1975 | Thornton, Jr. et al. | ......... 433/28 |
| 3,872,594 A | * | 3/1975 | Gerteisen | ..................... 433/166 |
| 4,775,320 A | * | 10/1988 | Marshall et al. | ............. 433/214 |
| 4,906,185 A | * | 3/1990 | Randklev | ....................... 433/8 |
| 5,927,976 A | * | 7/1999 | Wu | ............................. 433/82 |
| 6,093,084 A | * | 7/2000 | Jefferies | ...................... 451/37 |
| 6,149,430 A | * | 11/2000 | Nemetz et al. | ............. 433/132 |

* cited by examiner

*Primary Examiner*—John J. Wilson
(74) *Attorney, Agent, or Firm*—Michael Best & Friedrich LLP

(57) ABSTRACT

A method of finishing resin-based dental restorations by contouring and smoothing the surface of the dental restoration in a single step, using steel burs operating at low speed, high-torque.

6 Claims, 2 Drawing Sheets

METHOD OF FINISHING RESIN-BASED DENTAL RESTORATIONS

This application is based on and claims priority from U.S. Provisional Application Serial No. 60/250,560, filed Dec. 1, 2000.

FIELD OF THE INVENTION

The present invention relates to a method for finishing resin-based dental restorations for human teeth and, in particular, to a method for contouring and polishing resin-based dental restorations.

BACKGROUND OF THE INVENTION

The preparation of dental restorations for human teeth using resin-based materials, such as hybrid and microfill composites, compomers and similar materials, is well known in the art. The process of finishing such restorations—i.e., contouring and polishing the restorations to create a natural appearance—can be a time-consuming multi-step process, requiring the use of several different tools. Typically, the resin-based restoration is first subject to initial contouring, using a diamond or tungsten carbide bur to roughly reproduce the occlusal anatomy of the tooth (as shown in FIG. 1a). The restoration is then fine contoured, using a tungsten carbide finishing bur to blend the restoration into the tooth and to characterize the restoration by creating developmental grooves, lobes, ridges and other secondary and tertiary anatomy (as shown in FIG. 1b). Once the restoration has been appropriately contoured, it is then smoothed using rubber finishing instruments, such as rubber discs, cups and points (as shown in FIG. 1c). Finally, the restoration is polished to create an enamel-like finish, using diamond or aluminum oxide polishing pastes applied by rubber cups and points (as shown in FIG. 1d).

Fine contouring and smoothing are the most important steps in the process of finishing a resin-based restoration. Creating a smooth and accurately defined transition or margin between the resin and the tooth extends the life of the restoration by reducing general wear and minimizing the risk of microleakage, chipping, staining and other wear problems that may cause deterioration of the restoration and increase the risk of recurrent caries.

In general, the step of fine contouring a resin-based restoration is performed using tungsten carbide burs in connection with high-speed, low-torque handpieces. The operation of the bur at high speeds is thought to permit rapid removal of material, thereby reducing the treatment time and minimizing the generation of frictional heat. However, the use of high-speed burs requires a high level of skill and attention. High-speed tungsten carbide burs rapidly and aggressively remove resin and enamel, thereby increasing the risk of accidental damage to the restoration and/or enamel of the tooth.

In addition, the operation of the bur at low torque limits the amount of pressure that can be applied to the bur. The inadvertent application of excessive pressure can cause the bur to unexpectedly seize up and stop rotating. As a result, the operator may lose control of the bur, allowing the bur to slip and gouge or chatter across the surface of the restoration and tooth, causing damage to the restoration and enamel of the tooth. Furthermore, high-speed burs must be operated under a constant spray of water to avoid generating frictional heat, which may cause damage to the restoration and tooth. This spray of water also creates a mist which can obscure the working area. These problems involved in using high-speed, low-torque burs are particularly acute in the case of posterior restorations, which are difficult to access and visualize, and which typically involve the reproduction of complex anatomy requiring firm control over the bur.

Consequently, the step of fine contouring the restoration using high-speed, low-torque burs must be performed by removing the material in small steps, using light contact pressure to minimize the risk of inadvertently damaging the restoration or enamel of the tooth. As a result, the process of finishing restorations can be time consuming and tedious, requiring a high degree of skill and patience.

In addition, these operating conditions make it difficult for the operator to adequately control the bur during the step of fine contouring the restoration. In particular, the use of firm and continuous pressure is often required to permit the precise control of the bur needed to create a smooth and accurately defined margin between the resin and the tooth. The inability to fine contour an accurately defined margin cannot be corrected in the subsequent smoothing and polishing steps. The rubber instruments used in smoothing and polishing do not contour the resin, but merely smooth the already contoured surface of the restoration. Moreover, excessive working of the restoration using rubber instruments can cause the rubber to deteriorate, resulting in the incorporation of rubber particles into the surface of the resin. Finally, it is essential to be able to create smooth and accurately defined margins in the fine contouring step.

Thus, there is need for a method of finishing resin-based dental restorations which reduces the risk of inadvertent damage to the restoration and enamel of the tooth, by providing greater control over the bur and improved visualization of the work area during the step of fine contouring. Furthermore, there is a need for a method of finishing resin-based restorations which is less time consuming, and which requires fewer instruments and finishing steps.

SUMMARY OF THE INVENTION

These needs and other needs are satisfied by the present invention, which comprises a method of preparing a dental restoration using a resin based material wherein the steps of fine contouring the restoration and creating a smooth transition between the resin-based material and tooth are performed in a single step, using a low speed, high torque bur.

DETAILED DESCRIPTION OF THE INVENTION

Figure 1A:
FIG. 1a depicts the prior art step of initial contouring a resin-based restoration using a diamond bur.
Figure 1B:
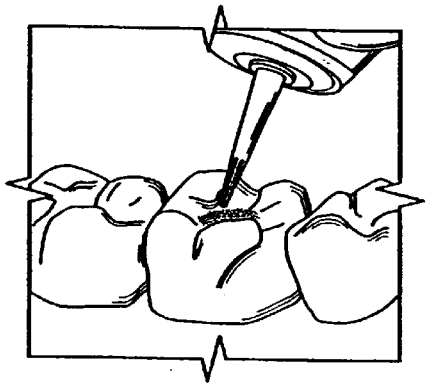
FIG. 1b depicts the prior art step of fine contouring a resin-based restoration using a tungsten carbide finishing bur.
Figure 1C:
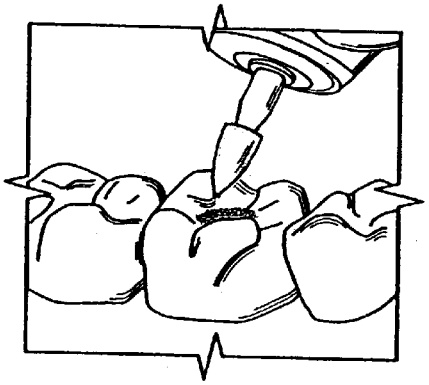
FIG. 1c depicts the prior art step of smoothing a resin-based restoration using a rubber point.
Figure 1D:
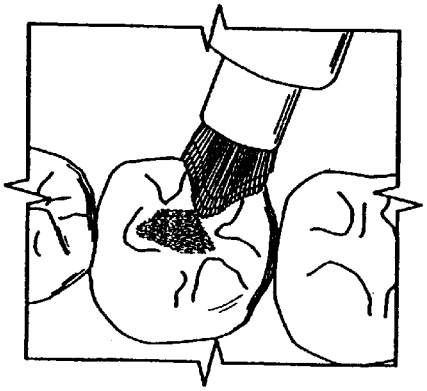
FIG. 1d depicts the prior art step of polishing a resin-based restoration using a rubber point.

In accordance with the present invention, a method of finishing resin-based dental restorations is described, using burs operated at low-speed, high-torque, which provides distinct advantages when compared to the prior art methods using high-speed, low-torque burs.

The method of the present invention comprises contouring and polishing resin-based restorations using burs operated at low-speed and high-torque, without the subsequent smoothing and polishing steps of prior art methods. Initial contouring of the restoration to reproduce the rough occlusal anatomy of the tooth is accomplished using a bur in connection with a low-speed, high-torque handpiece. As used herein, the term low-speed means operation at less than approximately 30,000 rpm, and preferably between approximately 12,000 rpm to 30,000 rpm. The term high torque means sufficient torque to maintain a constant speed between approximately 12,000 rpm to 30,000 rpm, when firm, continuous pressure is applied to the bur as the restoration is being contoured.

Burs used for contouring resin-based restorations are commercially available having from 8 to 30 flutes—the burs having a higher number of flutes providing a smoother finish and being more useful for fine contouring. Such burs are provided in a variety of shapes, each shape designed to perform a particular task in reproducing the various anatomical features of the restoration.

It is presently preferred to perform the step of initial contouring using a bur having from 8 to 16 flutes, to rapidly create the rough occlusal anatomy of the restoration. In general, the selection of the bur shape or shapes used in contouring the restoration is a function of the shape of the anatomy which must be reproduced and the preference of the individual operator.

Once the initial contours of the restoration have been formed, the restoration is then fine contoured to blend the restoration into the tooth and to characterize the restoration by reproducing secondary and tertiary anatomy, such as developmental grooves, lobes, ridges and other anatomy. The fine contouring step is performed using a low-speed, high-torque bur having at least approximately 20 flutes and, preferably, 30 flutes. Firm, continuous pressure is applied to the bur in forming the anatomy of the restoration and in defining the margin between the restoration and tooth.

It has been found that contouring resin-based restorations using low-speed, high-torque burs and applying firm, continuous pressure to the bur produces a burnishing effect on the resin material. The resulting contoured restoration has a smooth, enamel-like finish, such that the subsequent steps of smoothing and polishing the surface of the restoration are generally not required. As a result, the operator is able to accomplish the steps of contouring, smoothing and polishing in a single step, thereby dramatically reducing treatment time and the need to use multiple instruments, such as rubber smoothing and polishing instruments.

In contrast, the prior art method of contouring restorations using high-speed burs results in a cutting effect on the resin material, which produces fine ridges on the surface of the contoured restoration. This uneven surface is aesthetically unacceptable and, more importantly, makes the restoration less wear resistant and more susceptible to staining. Thus, the prior art methods of finishing restorations require the additional steps of smoothing and polishing the surface of the contoured restoration.

The method of the present invention using low-speed, high-torque burs further provides the operator with greater control over the bur in comparison to prior art methods. Because the bur operates at low speed, it removes material at a slower rate than prior art high-speed burs. As a result, the operator has more time to manipulate the bur and form fine anatomy. Moreover, because the burs of the present invention are operated at high-torque, the operator may exert firm pressure on the bur without the risk that the bur may seize up and cause the operator to lose control over the bur. Thus, the inventive method of operating burs at low-speed and high-torque allows the operator to contour the restoration using firm, continuous movements of the bur. This increased level of control over the bur is critical in forming smooth and accurately defined margins between the restoration and the enamel of the tooth.

In contrast, the prior art high-speed, low-torque burs remove material rapidly and aggressively, with a corresponding increase in the risk of inadvertent damage to the restoration and to the enamel of the tooth. In addition, the operation of the bur at low torque creates a further risk that the inadvertent application of excessive pressure on the bur may cause the bur to seize up and stop rotating. As a result, the operator may lose control over the bur, permitting the bur to slip and cause damage to the restoration and enamel of the tooth. To minimize these risks, prior art high-speed, low-torque burs must be used with light contact pressure to remove material in small steps, allowing the operator little time to manipulate the bur to form detailed anatomy and smooth, accurately defined margins.

More significantly, the prior art methods do not provide the operator with sufficient control over the bur to permit the firm, continuous movement of the bur required to produce smooth and accurately defined margins between the restoration and the enamel of the tooth. The inability to produce accurately defined margins cannot be corrected by subsequent smoothing and polishing using rubber instruments, which are incapable of contouring the restoration. Thus, the method of the present invention typically results in restorations with a superior finish in comparison to prior art methods.

In addition, the present method of using low-speed burs minimizes the generation of frictional heat, which may cause damage to the restoration and to the enamel of the tooth. Because low speed burs create less frictional heat than high-speed burs, the low-speed burs may be used without spraying the working surface of the restoration with water or air to prevent the buildup of heat, as is required by prior art methods using high-speed burs. This spray of water creates a mist which can obscure the working area, thereby increasing the risk of accidental damage to the restoration and to the enamel of the tooth. As a result, the use of prior art high-speed burs forces the operator to frequently pause during the contouring of the restoration to permit the progress of the work to be checked.

The advantages over the prior art methods provided by the use of low-speed, high-torque burs in the present invention significantly reduce the treatment time involved in finishing resin-based restorations. The present method provides the operator with increased control over the bur, permitting the bur to be used more surely with firm, continuous pressure and little risk of accidental damage to the restoration and the enamel of the tooth. Thus, although the prior art high-speed, low-torque burs remove material at a much more rapid rate, the corresponding loss of control over the bur and increased risk of accidental damage to the restoration and to the enamel of the tooth require the operator to exercise a much higher level of skill and attention during the contouring steps of finishing the restoration. As a result, the prior art methods of contouring resin-based restorations are much more time consuming and tedious in comparison to the method of the present invention. Moreover, the prior art methods require the operator to carry out the additional steps of smoothing and polishing the restoration, which are not required by the present invention.

It is presently preferred to use the inventive method in connection with hybrid and microfill composite restorations. Although such restorations finished in accordance with the present invention do not require additional polishing, it is possible that further polishing of the restoration may contribute to the aesthetic appearance of the restoration. Thus, in some circumstances, it may be desirable to enhance the polishing of the restoration using a diamond or aluminum oxide polishing paste and a rubber or felt instrument, such as when resin materials other than hybrid or microfill composites are used.

It is further preferred to fine contour the resin-based restoration using tungsten vanadium steel burs (commercially available from Busch & Co., Germany) having at least approximately 20 flutes and, preferably, 30 flutes. The relative softness of steel burs is believed to produce a superior burnishing effect in comparison to tungsten carbide burs having the same size and shape. This burnishing effect significantly enhances the ability of low-speed, high-torque burs to polish resin-based restorations. In addition, burs having a higher number of flutes produce a smoother and more polished finish.

Figure 2:
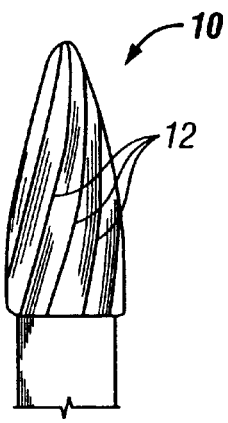
FIG. 2 is a side elevation view of a bur used with the present invention, having a flame-shape.
Figure 3:
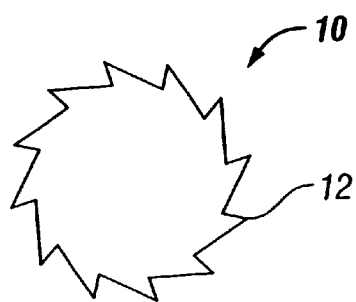
FIG. 3 is a horizontal section view of the bur of FIG. 2, wherein the flutes are angled toward the direction of rotation.
Figure 4:
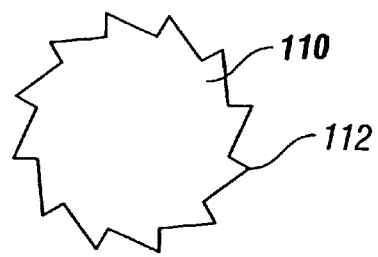
FIG. 4 is a horizontal section view of the bur of FIG. 2, in an alternative embodiment of the present invention, wherein the flutes are normal to the axis of rotation of the bur.
Figure 5:
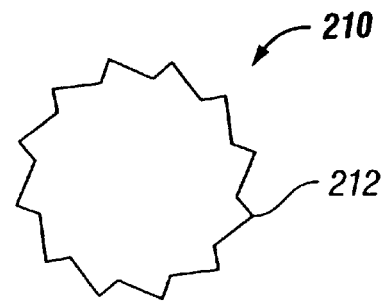
FIG. 5 is a horizontal section view of the bur of FIG. 2, in an alternative embodiment of the present invention, wherein the flutes are angled away from the direction of rotation.

In an alternative embodiment, tungsten carbide burs may be used to fine contour the restoration, which have a modified profile to increase the ability of the bur to burnish rather than cut resin-based restorations. For example, as shown on FIGS. 2 and 3, burs 10 are typically designed having flutes 12 that are angled toward the direction of rotation to increase the cutting action of the bur. It is believed that changing the profile of the bur, such that the flutes 112 are normal to the axis of the bur 110 (as shown in FIG. 4) or the flutes 212 are angled away from the direction of rotation of bur 210 (as shown in FIG. 5), increases the ability of the bur to burnish rather than cut resin-based restorations. The use of tungsten carbide provides increased wear resistance and corrosion resistance in comparison to steel. Thus, tungsten carbide burs are more wear resistant and may be repeatedly sterilized by autoclaving, in comparison to steel burs which typically must be discarded after one or two procedures and can be corroded by autoclaving.

Finally, it is possible to perform the step of initial contouring of the restoration using conventional methods employing tungsten carbide or diamond burs. However, in such cases it is necessary to ensure that the entire surface of the restoration produced by such conventional methods is subsequently fine contoured in accordance with the method of present invention. Thus, it is preferred to perform both the initial and fine contouring steps using steel burs or tungsten carbide burs having a modified profile to increase the burnishing effect, to avoid the risk that some areas of the surface of the restoration will not be completely finished.

It will be apparent to those skilled in the art that changes and modifications may be made in the embodiments illustrated herein, without departing from the spirit and the scope of the invention. Thus, the invention is not to be limited to the particular forms herein shown and described.

What is claimed is:

1. A method of finishing resin-based dental restorations, comprising the steps of:

preparing a dental restoration using a resin-based material;

fine contouring the restoration and creating a smooth transition between the resin-based material and tooth in a single step using a bur having between 8 to 30 flutes and operating at less than about 30,000 rpm and having sufficient torque to maintain a constant speed of about 12,000 to 30,000 rpm when firm, continuous pressure is applied to the resin-based material.

2. The method of claim 1, wherein said bur operates in a range of about 12,000 to 30,000 rpm.

3. The method of claim 1, wherein said bur has 20 to 30 flutes.

4. The method of claim 1, wherein said bur is made of steel.

5. The method of claim 1, wherein said bur is made of tungsten carbide.

6. The method of claim 5, wherein said flutes are normal to the axis of the bur or angled away from the direction of rotation.

* * * * *